US011673071B2

(12) United States Patent
Kambouris

(10) Patent No.: US 11,673,071 B2
(45) Date of Patent: Jun. 13, 2023

(54) ISOTOPIC COMPOSITIONS

(71) Applicant: Ambrosios Kambouris, Koorlong (AU)

(72) Inventor: Ambrosios Kambouris, Koorlong (AU)

(73) Assignee: BOTANICAL WATER TECHNOLOGIES IP LTD, London (GB)

( * ) Notice: Subject to any disclaimer, the term of this patent is extended or adjusted under 35 U.S.C. 154(b) by 0 days.

(21) Appl. No.: 16/334,253

(22) PCT Filed: Sep. 15, 2017

(86) PCT No.: PCT/AU2017/051005
§ 371 (c)(1),
(2) Date: Mar. 18, 2019

(87) PCT Pub. No.: WO2018/053578
PCT Pub. Date: Mar. 29, 2018

(65) Prior Publication Data
US 2019/0388310 A1    Dec. 26, 2019

(30) Foreign Application Priority Data
Sep. 21, 2016  (AU) .................. 2016903800

(51) Int. Cl.
*B01D 3/08*    (2006.01)
*A23L 2/02*    (2006.01)
(Continued)

(52) U.S. Cl.
CPC ............... *B01D 3/085* (2013.01); *A23L 2/02* (2013.01); *A23L 2/38* (2013.01); *A61K 8/22* (2013.01);
(Continued)

(58) Field of Classification Search
None
See application file for complete search history.

(56) References Cited

U.S. PATENT DOCUMENTS 3,870,606 A * 3/1975 Tabata .................. B01D 3/065
                                                       203/5
4,112,062 A    9/1978 Spevak
(Continued)

FOREIGN PATENT DOCUMENTS

| EP | 2910298 A1 | 8/2015 |
|----|------------|--------|
| RU | 2270590    | 2/2006 |

(Continued)

OTHER PUBLICATIONS

RU2287318 C2 (published in 2006): Google English Translation ([retrieved from on-line website: https://patents.google.com/patent/RU2287318C2/en, Mar. 25, 2020 ]) (Year: 2020).*
(Continued)

*Primary Examiner* — Kyung S Chang
(74) *Attorney, Agent, or Firm* — Sand, Sebolt & Wernow Co., LPA

(57) ABSTRACT

The present invention provides a beverage and a dermatological composition comprising water molecules, the water molecules having oxygen atoms of different isotopes, the beverage being enriched in at least one of the oxygen isotopes, the enrichment being in reference to (i) the amount of that oxygen isotope in the water used to produce the beverage or (ii) the amount of that oxygen isotope in ground water, or (iii) Vienna Standard Mean Ocean Water. The water molecules may be derived from a plant source, such as a juice, a sap or a tree water.

20 Claims, 1 Drawing Sheet

(51) Int. Cl.
- *A61K 8/22* (2006.01)
- *A61K 9/00* (2006.01)
- *A61K 33/00* (2006.01)
- *A61Q 19/00* (2006.01)
- *B01D 1/26* (2006.01)
- *B01D 3/14* (2006.01)
- *C01B 5/00* (2006.01)
- *C02F 1/04* (2023.01)
- *A23L 2/38* (2021.01)

(52) U.S. Cl.
CPC .......... *A61K 9/0014* (2013.01); *A61K 9/0095* (2013.01); *A61K 33/00* (2013.01); *A61Q 19/007* (2013.01); *B01D 1/26* (2013.01); *B01D 3/14* (2013.01); *C01B 5/00* (2013.01); *C02F 1/04* (2013.01); *A23V 2002/00* (2013.01)

(56) References Cited

U.S. PATENT DOCUMENTS

| | | | |
|---|---|---|---|
| 5,855,921 | A | 1/1999 | Somlyai |
| 6,321,565 | B1 | 11/2001 | Kihara et al. |
| 2003/0141177 | A1 | 7/2003 | Countz |
| 2008/0145507 | A1* | 6/2008 | Soloviev ................. C12C 5/002 426/592 |
| 2009/0008235 | A1* | 1/2009 | Goel ...................... B01D 3/002 203/41 |

FOREIGN PATENT DOCUMENTS

| | | |
|---|---|---|
| RU | 2287318 | 11/2006 |
| WO | 2005070438 | 8/2005 |
| WO | 2006085784 | 8/2006 |
| WO | 2006085785 | 8/2006 |

OTHER PUBLICATIONS

Oxygen Isotopes (Lecture 16, Appendix I: p. 359-361, published in 2014). (Year: 2014).*

Prasad, Brinda et al: "Enrichment of H2O17O from tap water, characterisation of the enriched water, and properties of several 17O-labeled compounds" Anal Chem 2011, 82, 231-239 Abstract: Table 1; Conclusion.

Yunianta, Ben-Li Zhang et al: "Stable isotope fractionation in fruit juice concentrates: Application to the authentication of grapes and orange products" J. Agric Food Chem. 1995, 43, 2411-2417. Abstract: Experimental; Conclusions.

Dunbar, John and Wilson, A T.: "Oxygen and hydrogen isotopes in fruit and vegetable juices" Plant Physical (1983) 72, 725-727. Whole documents.

Keitaro Kiyosawa: "Freezing point mixtures of H2O16O with H217O and those of acqueous CD3CH2OH and CH313CH2OH solutions" Journal of Solution Chemistry, vol. 33, No. 4, 2004, p. 322-328. Abstract; Fig. 1; whole document.

Allison, G.B., et al.: "The relationship between deuterium and oxygen-18 delta values in leaf water", Chemical Geology: Isotope Geoscience Station (1985).

* cited by examiner

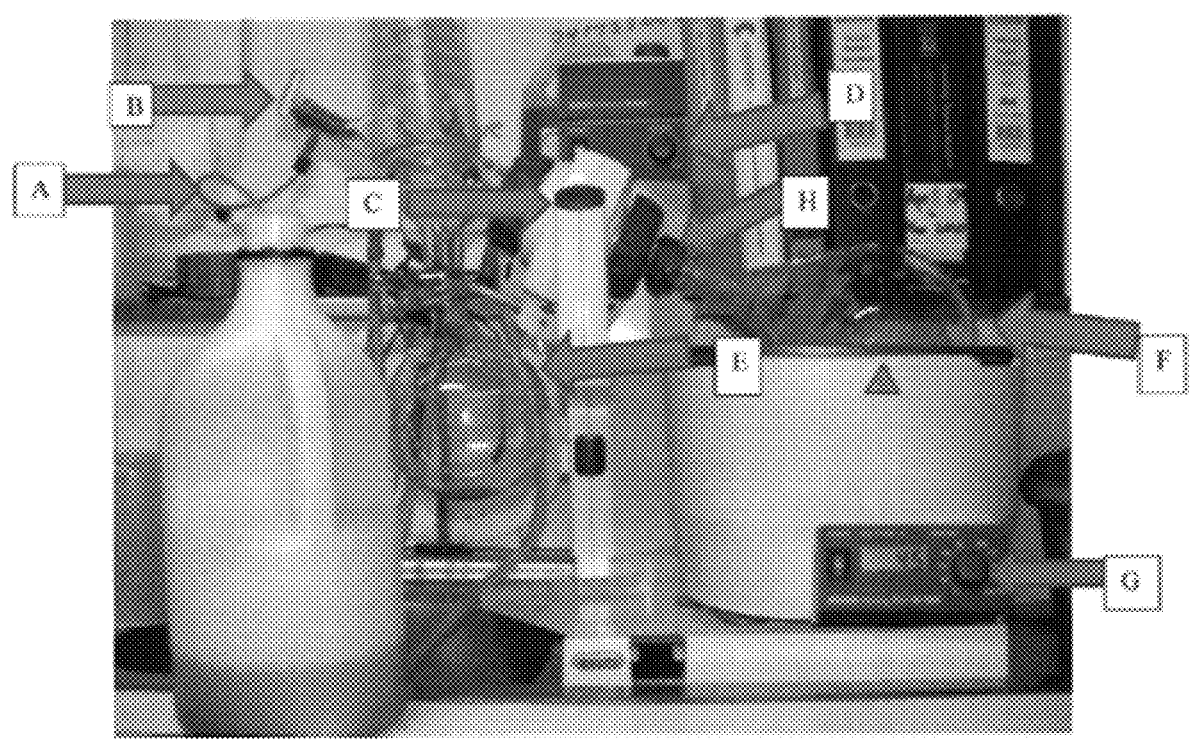

ISOTOPIC COMPOSITIONS

FIELD OF THE INVENTION

The present invention relates to the field of water-based compositions suitable for the hydration of a mammal, and particularly hydration of a human by oral or topical means.

BACKGROUND TO THE INVENTION

Water is a ubiquitous biological solvent, without which life cannot survive. Humans are particularly vulnerable to dehydration given that body temperature is modulated at least in part by sweating. While sweating is important for body temperature regulation it can also be a major source of water and solute loss. Maximum rate of sweating is up to 50 mls/min or 2,000 mls/hr in the acclimatised adult. This rate cannot be sustained, however losses up to 25% of total body water are possible under severe stress.

The prior art provides many different types of beverages formulated so as to replace water and electrolytes lost by way of sweating. Such beverages are typically consumed at or around a time of physical exertion. While generally effective, these beverages do not alter the amount of heat that can be carried away from the body given the fixed latent heat of evaporation of water.

Quite apart from the biological need for water, hydration in humans is also important for the skin having regard to function and aesthetic considerations. Under conditions of dehydration, the upper layers of the skin can become cracked, thereby creating a portal for the entry of infective agents. Dehydrated skin can also become irritated, leading to inflammatory responses that can lead to flushing and swelling of the skin. Furthermore, pathological conditions such as psoriasis can be exacerbated by dehydration of the skin.

With regard to aesthetic considerations, dehydrated skin loses plumpness and can take on a flaccid appearance. Any wrinkling of the skin appears more prominent, and the skin loses shine. A person having dehydrated skin often appears old or unhealthy.

In addressing aesthetic problems associated with skin dehydration, the prior art provides a vast range of hydrating topical compositions such as creams, gels lotions and the like which aim to infuse water molecules into the upper layers of skin. While generally effective in the short term, the rapid evaporation of water from the skin means that the skin soon returns to a state of lower hydration. These topical compositions may further comprise oils and other substances which aim to form a layer on the skin so as to limit water loss. However, the oils and other substances can act to block pores and congeal with makeup foundation and cosmetic facial powders.

It is an aspect of the present invention to overcome or ameliorate a problem of the prior art by providing improved beverages and topical compositions for the hydration of a mammal, and particularly a human. It is a further aspect to provide an alternative to prior art beverages and topical compositions.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

In a first aspect, but not necessarily the broadest aspect, the present invention provides a beverage comprising water molecules, the water molecules having oxygen atoms of different isotopes, the beverage being enriched in at least one of the oxygen isotopes, the enrichment being in reference to (i) the amount of that oxygen isotope in the water used to produce the beverage or (ii) the amount of that oxygen isotope in ground water, or (iii) Vienna Standard Mean Ocean Water.

In one embodiment of the beverage, the abundance of at least one isotope is:
 for isotope $16O$: 0.99757 mole fraction,
 for isotope $17O$: $3.8 \times 10^{-4}$ mole fraction, or
 for isotope $18O$: $2.05 \times 10^{-3}$ mole fraction In one embodiment of the beverage, the abundance of the at least one isotope is defined by the range:
 for isotope $16O$: 0.99738 to 0.99776 mole fraction,
 for isotope $17O$: $3.7 \times 10^{-4}$ to $4.0 \times 10^{-4}$ mole fraction, or
 for isotope $18O$: $1.88 \times 10^{-3}$ to $2.22 \times 10^{-3}$ mole fraction In one embodiment of the beverage, the abundance of the $17O$ isotope is less than $3.8 \times 10^{-4}$ mole fraction, and/or the abundance of the $18O$ isotope is less than $2.05 \times 10^{-3}$ mole fraction, and/or the abundance of the $16O$ isotope is greater than about 0.99757 mole fraction.

In one embodiment of the beverage, the abundance of the $17O$ isotope is less than $3.7 \times 10^{-4}$ mole fraction, and/or the abundance of the $18O$ isotope is less than $2.22 \times 10^{-3}$ mole fraction, and/or the abundance of the $16O$ isotope is greater than about 0.99776 mole fraction.

In one embodiment of the beverage, the delta-O-18 of the water molecules is greater than or less than about 0 0/00. In one embodiment of the beverage, the delta-O-18 of the water molecules is greater than about 5, 10, 15, 20, 25, 30, 35, 40, 45, 50, 55, 60, 65, 70, 75, 80, 85, 90, 95 or 100 0/00. In one embodiment of the beverage, the delta-O-18 of the water molecules is less than about −5, −10, −15, −20, −25, −30, −35, −40, −45, −50, −55, −60, −65, −70, −75, −80, −85, −90, −95 or −100 0/00.

In one embodiment of the beverage, the water molecules are derived from a water source, and the abundance of at least one of the oxygen isotopes being greater or less than the abundance of the at least one of the oxygen isotopes in the water source.

In one embodiment of the beverage, the water source is a tissue of a plant. In one embodiment of the beverage, the plant tissue is a reproductive or a vegetative tissue. In one embodiment of the beverage, the plant tissue is a fruit, a vegetable, a seed, a leaf, a stalk, or a root. The water source may also be a sap or a tree water of a plant.

In one embodiment of the beverage, the beverage comprises a food grade additive.

In one embodiment of the beverage, the additive is a colouring agent, a flavouring agent, an electrolyte, a sweetener, a preservative, a dissolved or undissolved gas, a nutrient, a vitamin, a pharmaceutical agent, a probiotic, or a prebiotic.

In another aspect, the invention provides a food grade vessel comprising the beverage as described herein.

In one embodiment, the vessel comprises a food grade lid forming a hermetic seal with the vessel.

In a further aspect, the present invention provides a topical dermatological composition comprising water molecules, the water molecules having oxygen atoms of different isotopes, the beverage being enriched in at least one of the oxygen isotopes, the enrichment being in reference to (i)

the amount of that oxygen isotope in the water used to produce the beverage or (ii) the amount of that oxygen isotope in ground water, or (iii) Vienna Standard Mean Ocean Water.

In one embodiment of the composition, the abundance of the at least one isotope is:
for isotope 16O: 0.99757 mole fraction,
for isotope 17O: 3.8×10−4 mole fraction, or
for isotope 18O: 2.05×10−3 mole fraction In one embodiment of the composition, the abundance of the at least one isotope is defined by the range:
for isotope 16O: 0.99738 to 0.99776 mole fraction,
for isotope 17O: 3.7×10−4 to 4.0×10−4 mole fraction, or
for isotope 18O: 1.88×10−3 to 2.22×10−3 mole fraction In one embodiment of the composition, the abundance of the 17O isotope is greater than 3.8×10−4 mole fraction, and/or the abundance of the 18O isotope is greater than 2.05×10−3 mole fraction, and/or the abundance of the 16O isotope is less than about 0.99757 mole fraction.

In one embodiment of the composition, the abundance of the 17O isotope is greater than 4.0×10−4 mole fraction, and/or the abundance of the 18O isotope is greater than 2.22×10−3 mole fraction, and/or the abundance of the 16O isotope is less than about 0.99738 mole fraction.

In one embodiment of the composition, the delta-O-18 of the water molecules is greater than or less than about 0 0/00. In one embodiment of the composition, the delta-O-18 of the water molecules is greater than about 5, 10, 15, 20, 25, 30, 35, 40, 45, 50, 55, 60, 65, 70, 75, 80, 85, 90, 95 or 100 0/00. In one embodiment of the composition, the delta-O-18 of the water molecules is less than about −5, −10, −15, −20, −25, −30, −35, −40, −45, −50, −55, −60, −65, −70, −75, −80, −85, −90, −95 or −100 0/00.

In one embodiment of the composition, the water molecules are derived from a water source, and the abundance of at least one of the oxygen isotopes being greater or less than the abundance of the at least one of the oxygen isotopes in the water source.

In one embodiment of the composition, the water source is a tissue of a plant. In one embodiment of the composition, the plant tissue is a reproductive or a vegetative tissue. In one embodiment of the composition, the plant tissue is a fruit, a vegetable, a seed, a leaf, a stalk, or a root. The water source may also be a sap or a tree water of a plant.

In one embodiment the composition comprises a dermatologically acceptable additive. In one embodiment of the composition, the additive is hypoallergenic.

In one embodiment of the composition, the additive is a colouring agent, a perfume, a salt, a buffer, a preservative, an emulsifier, an oil, a vitamin, a detergent, a dermatologically active agent, or a pharmaceutical agent.

In a further aspect the present invention provides a cosmetic grade vessel comprising the composition as described herein. In one embodiment, the vessel comprises a cosmetic grade lid forming a hermetic seal with the vessel.

In yet a further aspect, the present invention provides a method for producing a beverage or a topical dermatological composition, the method comprising the steps of: providing a water source, the water molecules having oxygen atoms of different isotopes, (i) fractionating the water source to produce a fraction enriched in water molecules having an abundance of at least one of the oxygen isotopes being greater or less than the abundance found in the water source, or (ii) where the water source is already enriched in heavy water, fully or partially maintaining the level of enrichment.

In one embodiment of the method, the step of fractionating comprises the step of evaporating the water source.

In one embodiment of the method, the step of fractioning comprises the step of concentration of the water source.

In one embodiment of the method, the water source is a tissue of a plant. In one embodiment of the method, the plant tissue is a reproductive or a vegetative tissue. In one embodiment of the method, the plant tissue is a fruit, a vegetable, a seed, a leaf, a stalk, or a root. The water source may also be a sap or a tree water of a plant.

In one embodiment of the method, the plant tissue is treated to form a plant tissue extract, the plant tissue extract being subject of step fractionation step. In one embodiment of the method, the plant tissue extract is substantially a liquid. In one embodiment of the method, the liquid is a juice. In one embodiment of the method, the fractionation step is carried out using a food concentrator/evaporator.

In one embodiment of the method, the fractionation step comprises an evaporation step and a condensation step. In one embodiment of the method, the evaporation step is carried out until at least about 90, 91, 92, 93, 94, 95, 96, 97, 98, or 99% of water in the water source is evaporated. In one embodiment of the method, the condensate is differentially collected. In one embodiment of the method, the evaporation step and the condensation step are carried out using a multiple-effect evaporator. In one embodiment of the method, the fractionation step comprises a freezing step.

In one embodiment of the method, the fractionation step is carried out until at least about 90, 91, 92, 93, 94, 95, 96, 97, 98, or 99% of water in the water source is frozen.

In one embodiment of the method, the unfrozen water is differentially collected.

In one embodiment of the method, the fraction step is configured to provide a first fraction and a second fraction, the abundance of at least one of the oxygen isotopes being greater than the abundance found in the water source in the first fraction, and the abundance of at least one of the oxygen isotopes being less than the abundance found in the water source in the second fraction.

In one embodiment of the method, the method is for producing a beverage, the method comprises the step of adding a food grade additive to the first or second fraction.

In one embodiment of the method, the additive is a colouring agent, a flavouring agent, an electrolyte, a sweetener, a preservative, a dissolved or undissolved gas, a nutrient, a vitamin, a pharmaceutical agent, a probiotic, or a prebiotic.

In one embodiment the method comprises the step of transferring the first or second fraction to a food grade vessel.

In one embodiment the method comprises the step of hermetically sealing the vessel.

In one embodiment of the method, where the method is for producing a topical dermatological composition, the method comprises the step of adding a dermatologically acceptable additive to the first or second fraction.

In one embodiment of the method for producing a topical dermatological composition, the additive is a colouring agent, a perfume, a salt, a buffer, a preservative, an emulsifier, an oil, a vitamin, a detergent, a dermatologically active agent, or a pharmaceutical agent.

In one embodiment of the method for producing a topical dermatological composition, the method comprises the step of transferring the first or second fraction to a cosmetic grade vessel.

In one embodiment of the method for producing a topical dermatological composition, the method comprises the step of hermetically sealing the vessel.

In some embodiments, the water source or a precursor of the water source, or an intermediate product is concentrated or fractionated by a method selected from the group consisting of a nanofiltration, reverse osmosis, forward osmosis, membrane distillation, or a methodology operating on the same or similar principle as any of the aforementioned methods.

Yet a further aspect of the present invention provides a method of treating or preventing dehydration or elevated temperature in a subject, the method comprising the step of administering to a subject in need thereof an effective amount of the beverage as described herein In one embodiment of the method of treatment, the elevated temperature is caused by physical activity or fever.

Yet a further aspect of the present invention comprises a method of treating or preventing dehydration or an aesthetic disorder of the skin of a subject, the method comprising the step of applying directly to the skin of a subject in need thereof an effective amount of the topical dermatological composition as described herein.

In one embodiment of the skin treatment method, the aesthetic disorder of the skin is skin laxity, wrinkles, skin flaking, skin dullness, or aged appearance.

BRIEF DESCRIPTION OF THE FIGURE

FIG. 1 shows an apparatus used for the laboratory scale preparation of isotopically enriched condensate.

DETAILED DESCRIPTION OF THE PRESENT INVENTION

After considering this description it will be apparent to one skilled in the art how the invention is implemented in various alternative embodiments and alternative applications. However, although various embodiments of the present invention will be described herein, it is understood that these embodiments are presented by way of example only, and not limitation. As such, this description of various alternative embodiments should not be construed to limit the scope or breadth of the present invention. Furthermore, statements of advantages or other aspects apply to specific exemplary embodiments, and not necessarily to all embodiments covered by the claims.

Throughout the description and the claims of this specification the word "comprise" and variations of the word, such as "comprising" and "comprises" is not intended to exclude other additives, components, integers or steps.

Reference throughout this specification to "one embodiment" or "an embodiment" or "some embodiments" means that a particular feature, structure or characteristic described in connection with the embodiment are included in at least one embodiment of the present invention. Thus, appearances of the phrases "in one embodiment" or "in an embodiment" or "in some embodiments" in various places throughout this specification are not necessarily all referring to the same embodiment, but may.

The present invention is predicated at least in part on Applicant's finding that water which is preferentially enriched in "heavy" water molecules (i.e. water molecules having oxygen atoms of isotopes with 17, 18 or more neutrons) or "light" water molecules (i.e. water molecules having oxygen atoms of isotopes with 16 or less neutrons) is useful in the hydration of a mammal both orally/parenterally, and also topically. Accordingly, in a first aspect the present invention provides a beverage comprising water molecules, the water molecules having oxygen atoms of different isotopes, the beverage being enriched in at least one of the oxygen isotopes, the enrichment being in reference to (i) the amount of that oxygen isotope in the water used to produce the beverage or (ii) the amount of that oxygen isotope in ground water, or (iii) Vienna Standard Mean Ocean Water. As used herein, the term "beverage" is intended to include any drink suitable for animal consumption, including substantially pure water products.

In a second aspect the present invention provides a topical dermatological composition comprising water molecules, the water molecules having oxygen atoms of different isotopes, the beverage being enriched in at least one of the oxygen isotopes, the enrichment being in reference to (i) the amount of that oxygen isotope in the water used to produce the beverage or (ii) the amount of that oxygen isotope in ground water, or (iii) Vienna Standard Mean Ocean Water. As used herein, the term "topical dermatological composition" is intended to include any composition suitable for application to the skin of an animal, including substantially pure water products.

The level of enrichment of any given oxygen isotope in the water of the beverage may be defined by reference to a comparison water. The comparison water may be the water used to produce the beverage which may be municipal water supply, or a natural water supply such as river water or spring water or rain water.

Alternatively, the comparison water is an isotopically neutral water such as ground water, or an isotopically standard water such as Vienna Standard Mean Ocean Water (VSMOW).

The enrichment may be calculated based on the total number of oxygen atoms for an isotope in the beverage compared with the total number of oxygen atoms in the comparison water. As a basic example to illustrate the principle: where the comparison water has 99 atoms of the isotope 16O and 1 atom of the isotope 18O (for a total of 100 atoms), and the beverage water has 98 atoms of 16O and 2 atoms 18O (for a total of 100 atoms) then the enrichment for 18O can be expressed as 1 molecule per 100 total molecules.

The level of enrichment may be at least about 1 molecule per 1000000 total molecules, 1 molecule per 100000 total molecules, 1 molecule per 10000 total molecules, 1 molecule per 1000 total molecules, 1 molecule per 900 total molecules, 1 molecule per 800 total molecules, 1 molecule per 700 total molecules, 1 molecule per 600 total molecules, 1 molecule per 500 total molecules, 1 molecule per 400 total molecules, 1 molecule per 300 total molecules, 1 molecule per 200 total molecules, 1 molecule per 100 total molecules, 1 molecule per 90 total molecules, 1 molecule per 80 total molecules, 1 molecule per 70 total molecules, 1 molecule per 60 total molecules, 1 molecule per 50 total molecules, 1 molecule per 40 total molecules, 1 molecule per 30 total molecules, 1 molecule per 20 total molecules or 1 molecule per 10 total molecules.

The enrichment of heavy water molecules or light water molecules may be set at a predetermined level, or toward a predetermined level, or in accordance with a desired result. For example, where a beverage is to be used to facilitate sweating to decrease body temperature during physical exertion, the beverage water may be enriched for light water molecules. Applicant proposes that light water molecules secreted in sweat evaporate from the skin surface more easily, and are therefore have a higher capability of removing the latent heat of vaporisation from the skin as compared with heavy water molecules. Removal of the latent heat of vaporisation acts to cool the skin, and assist in maintaining or decreasing body temperature. By contrast, a beverage enriched in heavy water molecules may be used where water loss from the skin surface is to be avoided, for example to improve hydration of the skin for functional or cosmetic reasons, or to otherwise avoid water loss from the body.

In the case of a topical dermatological composition, the water molecules may be enriched in heavy water so as to avoid evaporation of water from the skin. Thus, the composition is deposited on the surface of the skin (by a spray, of by manual application) thereby forming a film of water molecules over the skin. The film is enriched in heavy water molecules and so has a lower propensity for evaporation. The skin therefore remains hydrated to a greater level and/or for a greater time period as compared with a composition not enriched in heavy water molecules.

In some situations, a dermatological composition enriched in light water molecules may be required. As an example, the composition may be a spray which is intended to assist in cooling the body in hot weather. In that case, the light water molecules are more likely to evaporate than heavy water molecules, and therefore more capable of removing the latent heat of vaporization from the skin.

The source of water from which the beverage or dermatological composition is produced may be naturally enriched in heavy water or light water. For example, water molecules present ground water, surface water, sea water, lakes, rivers, precipitation, snow, ice derived from precipitation, and glacial ice will all have differing ratio of heavy water molecules to light water molecules. The ratio also varies according to the location of the water source, and in particular the atmospheric temperature of the location. In the context of the present invention the water molecules used to produce the dermatological compositions or the beverages may be obtained from a natural source which is already enriched with heavy or light water molecules. In other embodiments, the water used to produce the dermatological compositions or the beverages is modified by any means deemed useful by the skilled artisan to result in an enrichment of at least one oxygen isotope.

The level of enrichment of heavy water to light water molecules may be expressed by reference to means known in the meteorological, geochemical, paleoclimatological and paleocenanographical arts by reference to a the delta-18-O value. This value is a measure of the ratio of stable isotopes 18O:16O, and is commonly used as a measure of the temperature of precipitation, as a measure of groundwater/mineral interactions, and as an indicator of processes that show isotopic fractionation, such as methanogenesis. In paleosciences, 18O:16O data from corals, foraminifera and ice cores are used as a proxy for temperature. The definition is, in "per mil" (‰, parts per thousand), and calculated as follows:

$$\delta^{18}O = \left( \frac{\left(\frac{^{18}O}{^{18}O}\right)_{sample}}{\left(\frac{^{18}O}{^{18}O}\right)_{standard}} - 1 \right) * 1000\%_o$$

where the standard has a known isotopic composition, such as Vienna Standard Mean Ocean Water (VSMOW). A consideration of delta-18-O was hitherto unknown in the medical, cosmetic, or beverage production arts, however Applicant proposes that the value has use in describing the present beverages, compositions and methods.

Methods for determining delta-18-O are well known to persons skilled in the meteorological, geochemical, paleoclimatological and paleocenanographical arts, and the Applicant has found such methods to be useful also in the dermatological, cosmetic, or beverage production arts. Commercially available analysis units such as the model L2140-I (Picarro Inc, CA) provide high precision measurements of delta-18-O in water for applications such as paleoclimatology and oceanography. Applicant proposes that such instruments are useful also in the beverage, medical and cosmetic arts.

Given the benefit of the present specification, the skilled person is enabled to select a minimum level of heavy or light water molecule enrichment for a particular application. For some applications, the level of enrichment may be within the range of naturally occurring water while for others it may be necessary to deliberately enrich to greater levels than that found in nature.

In some embodiments, the water source may be substantially unenriched in heavy or light water molecules, or insufficiently enriched in heavy or light water molecules in consideration of the proposed use as a beverage or dermatological composition. In such circumstances, the water source may be fractionated by human intervention so as to provide a water enriched (or better enriched) in either heavy or light water molecules. Indeed, for reasons of convenience, or economy, or reproducibility the present compositions and beverages preferably contain water which has been artificially enriched in heavy or light water molecules.

In some embodiments of the invention, the source water is treated by an evaporative method. In such methods it is typical that the water is heated (optionally under vacuum) so as to cause evaporation of water molecules from the surface, and then condensing the evaporated water back to liquid water which is then collected for use in the beverage or the dermatological composition. Light water molecules preferentially evaporate, and so the condensate will be enriched in light water molecules. The unevaporated water remaining will be enriched in heavy water due to the exit of light water molecules.

In some embodiments, the water source is a plant tissue. Applicant proposes that significant advantage is provided by the use of plant tissue. One advantage is the heavy or light water that is collected comprises plant-derived ions and compounds. Fruit, vegetables and other plant materials contain phytonutrients, antioxidants, nutraceutical substances, minerals and vitamins and the like. A number of studies have demonstrated protection against chronic diseases such as heart disease, stroke, cancer and hypertension.

There are numerous types of phytonutrient types found in plant material, including alkaloids, betalains, carotenoids, chlorophyll and chlorophyllin, flavanoids, flavonoligans, Isothiocyanates, monoterpenes, organosulfides, phenolic compounds, sapanins and sterols.

Plant materials also contain water soluble vitamins such as vitamins C, B1, B2, niacin, B6, folate, B12, biotin and pantothenic acid. Water-soluble vitamins are not stored and are readily eliminated in the urine. Humans therefore require a continuous supply in the diet. Water soluble vitamins are available in many plant materials but are easily destroyed as a result of heating, exposure to air, alkaline or acidic conditions and light.

Eight of the water-soluble vitamins are known as the B-complex group: thiamin (vitamin B1), riboflavin (vitamin B2), niacin, vitamin B6, folate, vitamin Bi2, biotin and pantothenic acid. These vitamins are widely distributed in plant material. Their actions are exerted in many parts of the body, functioning as coenzymes involved in the extraction of energy from food. They also are important for appetite, vision, skin, nervous system and red blood cell formation.

Vitamin C assists in maintaining cell integrity, aids in wound healing, bone and tooth formation, strengthens the blood vessel walls, is vital for the function of the immune system, and improves absorption and utilization of iron. This vitamin also helps prevent nutritional ailments such as scurvy. Vitamin C also serves as an antioxidant, working with vitamin E as a free-radical scavenger. Studies suggest that vitamin C may reduce the risk of certain cancers, heart disease and cataracts. Vitamin C is not manufactured by the body, but must be constantly consumed. While the body has a constant need for vitamin C, it has a limited storage capacity. Accordingly, a beverage produced by a water that is enriched in heavy or light water molecules may provide further advantage to the consumer even if only trace amounts of any of the aforementioned compounds co-fractionate with a heavy or light water enriched fraction.

In the context of a topical dermatological composition, plant derived ions and compounds can provide functional or aesthetic advantage to the skin. Compounds such as vitamins are known to be useful in improving the function of appearance of skin. For example, vitamin C (from citrus fruits) and vitamin A (from carrot) have established roles in positively altering the skin to reduce wrinkles, irregular pigmentation and the like. Vitamin E (from broccoli, spinach, *papaya*, or avocado) is a potential free radical scavenger which protections skin from damaging oxidation. Vitamin K (from kale, onion, or asparagus) is effective in spider veins, scars, and dark circles under the eyes). Biologically active molecules in *Aloe* plant species are known to be beneficial for psoriasis.

Another advantage of using plant material as a source of water relates to the finding that plant-derived water is already enriched in heavy water molecules as compared with the water with which the plant has been grown. In the process of transpiration, water moves from the plant roots and exits via stomata on leaves and other structures. Light water molecules are more likely to be lost to the environment during transpiration (via the stomata) and so water remaining in the plant becomes enriched in heavy water molecules. Thus, plant-derived water (being already enriched in heavy water) useful as a beverage base, and also as a dermatological composition base. As a beverage base, the plant-derived water may be used to provide water to a person that wishes to reduce sweating and retain more water in the body. As a dermatological composition base, the heavy water is useful to provide a film over the skin which is less susceptible to evaporation.

Applicant has discovered that in extracting water from plant material that some or all of the beneficial heavy water fraction is lost in the extraction process. Accordingly, the extracted water is not useful, or is less useful, in the production of beverages or topical dermatological compositions. Thus, where an evaporative method is used to extract plant-derived water from a juice, for example, the extracted water does not comprise the number of heavy water molecules that would be expected given the number of heavy water molecules in the juice. Instead, much of the heavy water molecules appear to be lost.

Plant-derived water is often obtained as a by-product in prior art juice concentration methods. However, the by-product water has been found to be lower than expected in heavy water molecules It has been found that in order increase the yield of heavy water molecules, the evaporation process must be continued to a greater extent than would otherwise be undertaken. In prior art juice concentration methods, the juice is only partially concentrated with a significant amount of water remaining in the concentrate. For example, in commercial orange juice concentration operations the starting juice material has a water content of around 90% which is reduced by evaporation down to around 30%. Accordingly, a significant volume of water remains in the concentrate after the evaporation process. Even where the juice of sugar cane is highly concentrated to molasses, the water content of the product can be as low as 15%. However, Applicant proposes that the water remaining in the concentrate after the evaporation process is a source of heavy water molecules useful for the production of beverages and dermatological compositions.

Accordingly, it is proposed that concentration proceed to a greater extent to that usually undertaken in the preparation of juice concentrates such that the water content of the concentrate is less than about 30, 25, 20, 15, 10, 9, 8, 7, 6, 5, 4, 3, 2 or 1%. In this way, all our substantially all heavy water molecules are evaporated and then collected by way of condensate. Thus, little or no heavy water molecules are lost. We evaporation to the point of leaving substantially solid material is required, specialized equipment may be used in order to extract the last remnants of water which will be particularly rich in heavy water molecules.

Where evaporation down to a solid is required, this may be achieved by any means deemed suitable by the skilled person so long as any water removed can be recovered. For example, further heating in a vessel so as to drive off any remaining water may be implemented, with the final amounts of water being collected by a cooled condenser apparatus.

Alternatively, a commercial spray drying process may be used, optionally of the type known to those skilled in the art of food processing or pharmaceutical manufacture. In such embodiments, the water removed during the spray drying process may be condensed so as to provide a water enriched in heavy isotopic forms of water.

Where water which is very highly enriched in heavy water molecules is required, the condensate may be divided into condensate fractions, each fraction taken at subsequent stages of the evaporation process. Thus, the first fractions will comprise lower levels of heavy water molecules and the later fractions will comprise higher levels of heavy water molecules. For example, in an evaporation process the juice may be concentrated down to a water content of 20%, with the condensate being discarded or used for other purposes. The condensate obtained by way of further concentration from 20% to 5% is retained and used for a beverage or a dermatological composition due to the particularly high level of heavy water molecules.

Evaporative concentrators are known to persons skilled in the art of beverage concentrators, including multi-effect evaporator and concentrators. Suppliers of such equipment include Alfa Laval AB (Sweden) and Andritz AG (Austria).

As an alternative, or in addition to an evaporation method, source water may be fractionated be a freezing method. Without wishing to be limited by theory in any way, it is proposed that the lower activation energy and molecular weight of light water allows for light water to form ice more readily. Accordingly, were the source water is not complete frozen the unfrozen fraction will be enriched in heavy water and the frozen fraction enriched in light water. Either frozen or unfrozen fraction may be removed from the mixture as used as required.

In some embodiments, the water source or a precursor of the water source, or an intermediate product is concentrated or fractionated by a method selected from the group consisting of a nanofiltration, reverse osmosis, forward osmosis, membrane distillation, or a methodology operating on the same or similar principle as any of the aforementioned methods.

Formulation of Enriched Water into a Beverage

While the water enriched with either heavy or light water molecules may be used without further modification, additives may be added in some embodiments. For example where the beverage is a sports drink, electrolytes, buffers, food acids, food bases, colouring, flavouring, and sweetener may be added to the enriched water.

Where the beverage is an energy drink, compounds such as caffeine or guarana extract may be added.

Where the beverage is a soft drink, sugar, colourings and flavourings may be added and the mixture then carbonated.

Where the beverage is for nutritional, functional, therapeutic, nutraceutical, paramedical, quasi medical or medical indications the beverage may comprise an additive such as a carbohydrate, an amino acid, a peptide, a protein, a protein hydrosylate, a vitamin, a mineral, a fat, an oil, a plant extract, a probiotic, a prebiotic or an animal extract.

In some embodiments, the beverage may be used in the administration of a pharmaceutical substance, with the pharmaceutical substance being dissolved or suspended in the beverage. It is proposed that the administration of some pharmaceutically active substances is benefitted by solubilisation or suspension with a beverage enriched in heavy water molecules, given the lower propensity for such molecule to be lost through sweating or by evaporation from the surface of the lungs or the mouth. The heavy water molecules may form a hydration shell around an active compound, thereby preventing loss of the compound.

Where the beverage is a drink mixer, the beverage may only be carbonated.

Packaging of Beverage

The beverage may be presented in the form of a drink vessel, which may have a closure (such as a lid) capable of sealing the vessel. The vessel may have a volume of less than about 1000 ml, 900 ml, 800 ml, 700 ml, 700 ml, 600 ml, 500 ml, 400 ml, or 300 ml. The vessel may be labelled with a graphic, a trademark, text (including compositional analysis, and instructions for use).

Formulation of Enriched Water into Topical Dermatological Composition

The enriched water may be used without additives (for example, as a simple spray to hydrate the skin) of may be formulated into a composition having an additive such as a dermatologically acceptable excipient.

As used herein, the term "dermatologically acceptable excipient" includes without limitation any adjuvant, carrier, glidant, diluent, preservative, dye/colorant, surfactant, wetting agent, dispersing agent, suspending agent, stabilizer, isotonic agent, solvent, or emulsifier, including those approved by the United States Food and Drug Administration as being acceptable for dermatological or therapeutic use on humans, or which are known, or are suitable for use in dermatological compositions.

The composition is preferably formulated so as to minimise skin irritation will still ensuring an appropriate hydration of the skin, and/or the transport of active compounds into the skin.

As required, and with the benefit of the present specification the skilled person is enabled to decide whether or not any buffer or salt is required to provide a required pH or ionic strength for the composition. Acceptable salts include those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

The pH of the dermatological composition may be adjusted, optionally to between about 6.0 and 8.0 using an acid, such as a food acid. The acid for adjusting the pH value can be any conventionally used organic or inorganic acid or mixtures thereof, and is preferably citric acid.

Furthermore, a buffering agent may be included so as to maintain pH at a predetermined level. Useful agents for adjusting pH, buffering or otherwise altering the ionic conditions of a composition include (by name, CAS No., ELINCS No); 1,6-hexanediamine 124-09-4,204-679-6; 2-aminobutanol, 96-20-8, 202-488-2; acetic acid, 64-19-7, 200-580-7; acetyl mandelic acid, 51019-43-3/7322-88-5; adipic acid, 124-04-9, 204-673-3; alstonia scholaris bark extract, 91745-20-9, 294-689-7; aluminum glycinate, 13682-92-3/41354-48-7; aluminum lactate, 18917-91-4, 242-670-9; aluminum triformate, 7360-53-4,230-898-1; aminoethyl propanediol, 115-70-8, 204-101-2; aminomethyl propanediol, 115-69-5, 204-100-7; aminomethyl propanol, 124-68-5, 204-709-8; aminopropanediol, 616-30-8, 210-475-8; ammonia, 7664-41-7; 231-635-3; ammonium acetate 631-61-8, 211-162-9; ammonium bicarbonate, 1066-33-7, 213-911-5; ammonium carbamate, 1111-78-0, 214-185-2; ammonium carbonate, 10361-29-2, 233-786-0; ammonium chloride, 12125-02-9, 235-186-4; ammonium glycolate 35249-89-9; ammonium hydroxide, 1336-21-6, 215-647-6; ammonium lactate, 515-98-0, 208-214-8; ammonium molybdate 12054-85-2; ammonium nitrate 6484-52-2, 229-347-8; ammonium phosphate, 7722-76-1, 231-764-5; ammonium thiocyanate, 1762-95-4, 217-175-6; ammonium vanadate, 7803-55-6, 232-261-3; ascorbic acid, 50-81-7/62624-30-0, 200-066-2/263-644-3; azelaic acid, 123-99-9; 204-669; babassu acid; bakuhan; benzilic acid, 76-93-7, 200-993-2; bis-hydroxyethyl tromethamine, 6976-37-0, 230-237-7; bismuth citrate, 813-93-4, 212-390-1; boric acid, 10043-35-3/11113-50-1, 233-139-2/234-343-4; butyl diethanolamine, 102-79-4, 203-055-0; calcium carbonate, 471-34-1, 207-439-9; calcium citrate 813-94-5, 212-391-7; calcium dihydrogen phosphate, 7758-23-8, 231-837-1; calcium glycinate, 35947-07-0, 252-809-5; calcium hydroxide, 1305-62-0; 215-137-3; calcium lactate, 814-80-2, 212-406-7; calcium oxide, 1305-78-8, 215-138-9; calcium phosphate, 7758-23-8/10103-46-5, 231-837-1/233-283-6; citric acid 77-92-9/5949-29-1, 201-069-1; clay minerals; copper glycinate, 32817-15-5, 251-238-9; diammonium citrate, 3012-65-5, 221-146-3; diammonium phosphate, 7783-28-0, 231-987-8; dibutyl ethanolamine, 102-81-8, 203-057-1, diethyl ethanolamine, 100-37-8, 202-845-2; dimethyl isopropanolamine, 108-16-7, 203-556-4; dimethyl mea, 108-01-0, 203-542-8; dioleoyl edetolmonium methosulfate, 111030-96-7; dioleyl phosphate, 14450-07-8,238-431-3; dipotassium phosphate, 7758-11-4, 231-834-5; disodium fumarate, 17013-01-3, 241-087-7; disodium phosphate, 7558-79-4/7782-85-6, 231-448-7; disodium pyrophosphate, 7758-16-9, 231-835-0; disodium tartrate,868-18-8, 212-773-3; ethanolamine, 141-43-5, 205-483-3; ethanolamine HCL, 2002-24-6, 217-900-6; ethyl ethanolamine, 110-73-6, 203-797-5; fumaric acid, 110-17-8, 203-743-0; galacturonic acid, 685-73-4, 211-682-6; glucoheptonic acid, 23351-51-1, 245-601-0; gluconic acid, 526-95-4, 208-401-4; glucuronic acid, 576-37-4; 209-401-7; glutaric acid, 110-94-1, 203-817-2; glycine, 56-40-6, 200-272-2; glycolic acid, 79-14-1 201-180-5; glyoxylic acid, 298-12-4, 206-058-5; guanidine carbonate, 593-85-1, 209-813-7; guanidine HCl, 50-01-1, 200-002-3; hydrobromic acid, 10035-10-6, 233-113-0; hydrochloric acid, 7647-01-0, 231-595-7; hydroxyectoin, 165542-15-4, 442-870-8; hydroxyethylpiperazine ethane sulfonic acid, 7365-45-9, 230-907-9; imidazole, 288-32-4, 206-019-2; isobutyric acid, 79-31-2, 201-195-7; isopropanolamine, 78-96-6, 201-162-7; isopropylamine 75-31-0200-860-9; lactic acid, 50-21-5, 200-018-0; lactobionic acid, 96-82-2, 202-538-3; lauryl p-cresol ketoxime, 50652-76-1; lithium carbonate, 554-13-2, 209-062-5; lithium hydroxide, 1310-65-2, 215-183-4; magnesium acetate, 142-72-3, 205-554-9; magnesium carbonate hydroxide, 12125-28-9, 235-192-7; magnesium glycinate, 14783-68-7, 238-852-2; magnesium hydroxide, 1309-42-8, 215-170-3; magnesium lactate, 18917-93-6, 242-671-4; magnesium oxide, 1309-48-4, 215-171-9; maleic acid, 110-16-7, 203-742-5; malic acid, 97-67-6, 202-601-5; malonic acid, 141-82-2, 205-503-0; maltobionic acid 534-42-9; mea-borate, 10377-81-8, 233-829-3; metaphosphoric acid, 37267-86-0, 253-433-4; methoxy peg-100/polyepsilon caprolactone ethylhexanoate; methoxypeg-100/polyepsilon caprolactone palmitate; methoxy peg-114/polyepsilon caprolactone; methylethanolamine, 109-83-1, 203-710-0, monosodium citrate, 18996-35-5, 242-734-6; mudstone powder; *paecilomyces japonica*/grape/cucumber juice extract ferment filtrate; pentapotassium triphosphate, 13845-36-8, 237-574-9; pentasodium triphosphate, 7758-29-4, 231-838-7; phenolsulfonphthalein, 143-74-8, 205-609-7; phenyl mercuric borate, 102-98-7, 203-068-1; phosphonobutanetricarboxylic acid, 37971-36-1, 253-733-5; phosphoric acid, 7664-38-2, 231-633-2; phosphorus pentoxide, 1314-56-3, 215-236-1; potassium bicarbonate, 298-14-6, 206-059-0; potassium biphthalate, 877-24-5, 212-889-4; potassium bitartrate, 868-14-4, 212-769-1; potassium borate, 1332-77-0, 215-575-5; potassium carbonate, 584-08-7, 209-529-3; potassium citrate, 866-84-2, 212-755-5; potassium hydroxide, 1310-58-3, 215-181-3; potassium lactate, 996-31-6/85895-78-9, 213-631-3/288-752-8; potassium magnesium aspartate, 67528-13-6; potassium oxide, 12136-45-7, 235-227-6; potassium phosphate, 7778-77-0/16068-46-5, 231-913-4/240-213-8; potassium sodium tartrate, 304-59-6, 206-156-8; potassium tartrate, 921-53-9, 213-067-8; propane tricarboxylic acid, 99-14-9/51750-56-2, 202-733-3; quinic acid, 77-95-2/562-73-2/36413-60-2, 201-072-8/209-233-4; ribonic acid, 17812-24-7; sebacic acid, 111-20-6, 203-845-5; sesquiethoxytriethanolamine; sh-decapeptide-7; sodium acetate, 127-09-3, 204-823-8; sodium aluminate, 1302-42-7, 215-100-1; sodium aluminum lactate, 68953-69-5, 273-223-6; sodium arachidate; sodium aspartate, 17090-93-6/3792-50-5, 241-155-6/223-264-0; sodium bicarbonate, 144-55-8, 205-633-8; sodium bisulfate, 7681-38-1, 231-665-7; sodium borate, 1330-43-4/1303-96-4 215-540-4; sodium butoxyethoxy acetate, 67990-17-4, 268-040-3; sodium calcium boron phosphate; sodium calcium copper phosphate; sodium calcium zinc phosphate; sodium carbonate, 497-19-8, 207-838-8; sodium citrate, 68-04-2/6132-04-3, 200-675-3; sodium esylate, 5324-47-0, 226-194-9; sodium formate, 141-53-7, 205-488-0; sodium fumarate 5873-57-4/7704-73-6, 227-535-4/231-725-2; sodium glycolate, 2836-32-0, 220-624-9; sodium humate, 68131-04-4; sodium hydroxide, 1310-73-2, 215-185-5; sodium lactate, 72-17-3/867-56-1, 200-772-0/212-762-3; sodium metaphosphate, 10361-03-2/50813-16-6, 233-782-9/256-779-4; sodium metasilicate, 6834-92-0, 229-912-9; sodium oxide, 1313-59-3, 215-208-9; sodium phosphate, 7558-80-7/7632-05-5, 231-449-2/231-558-5; sodium sesquicarbonate, 533-96-0, 208-580-9; sodium silicate, 1344-09-8, 215-687-4; sodium succinate, 2922-54-5, 220-871-2; sodium trimetaphosphate, 7785-84-4, 232-088-3; strontium hydroxide 18480-07-4/1311-10-0, 242-367-1; succinic acid, 110-15-6; 203-740-4 sulfuric acid, 7664-93-9, 231-639-5; tartaric acid, 133-37-9/147-71-7/87-69-4,205-105-7/205-695-6/201-766-0; taurine, 107-35-7, 203-483-8; tea-diricinoleate/ipdi copolymer, 351425-02-0; tea-hydroiodide 7601-53-8, 231-508-2; tea-sulfate, 7376-31-0, 230-934-6; tetrahydroxyethyl ethylenediamine, 140-07-8, 205-396-0; tetrapotassium pyrophosphate, 7320-34-5, 230-785-7; tetrasodium pyrophosphate, 7722-88-5, 231-767-1; triethanolamine, 102-71-6, 203-049-8; triisopropanolamine, 122-20-3, 204-528-4; trisodium phosphate; 7601-54-9, 231-509-8; trisodium sulfosuccinate, 13419-59-5, 236-524-3; *Triticum vulgare* protein, 100684-25-1, 309-696-3; *Triticum vulgare* seed extract, 84012-44-2, 281-689-7; tromethamine, 77-86-1, 201-064-4; urea, 57-13-6, 200-315-5; uric acid, 69-93-2, 200-720-7; zinc carbonate hydroxide, 150607-22-0; zinc glycinate, 14281-83-5, 238-173-1; zinc hexametaphosphate, 13566-15-9, 236-967-2; and zinc magnesium aspartate.

Where a surfactant is included, the surfactant can be any conventionally used anionic, cationic, nonionic, zwitterionic or amphoteric surfactant or mixtures thereof.

The composition may be formulated as a simple aqueous solution/suspension but may also be formulated with the assistance is a viscosity-increasing agent such as a gum, a gel, an agar, or a hydrogel.

The present compositions may be formulated as a cream (with an aqueous or non-aqueous base, or a mixed base—oil in water or water in oil), a foam, a foaming solution, a lotion, a balm, a soap, a serum, or a cleanser.

In some embodiments, the dermatological composition is used in the administration of a dermatologically active substance such as a transdermal pharmaceutical substance. Where the composition is enriched in heavy water, the pharmaceutical substance may remain in solution for longer (given the lower rate of evaporation from the skin) and/or contacting the skin for a longer period of time.

In some embodiments, the water source or a precursor of the water source, or an intermediate product is concentrated or fractionated by a method selected from the group consisting of a nanofiltration, reverse osmosis, forward osmosis, membrane distillation, or a methodology operating on the same or similar principle as any of the aforementioned methods.

Packaging of Topical Dermatological Composition.

The composition may be presented in the form of a spray vessel configured to dispense a fine mist over the skin to provide a thin film of composition. Where the composition is viscous (such as in the form of a cream or a lotion) the vessel may be in the form of a tube, a bottle, a sachet, or a jar and have a closure capable of sealing the vessel. The vessel may be labelled with a graphic, a trademark, text (including compositional analysis, and instructions for use).

Where the composition is to be applied to the face only, and packages of relatively small volume will be useful, such as less than 100 ml, 90 ml, 80 ml, 70 ml, 60 ml, 50 ml, 40 ml, 30 ml, 20 ml and 10 ml.

The dermatological composition may be used to impregnate a wipe, with the wipe being sealed within a sachet. Alternatively, a plurality of wipes may be interleaved and packaged in a container capable of being sealed after removal of a wipe for use. Such wipes may be useful for make-up removal or as an infant wipe; in which case the composition used to impregnate the wipe may comprise a detergent, a soap, a cleanser, a mild exfoliant, a fragrance, an antibacterial, an anti-inflammatory, a skin demulcent, or the like.

The present compositions are typically implemented by the user by spraying, spreading, gently rubbing or massaging the composition onto the skin of an animal. In the context of the present invention the term "animal" is intended to include without limitation any mammal such as a human, primate, domestic animal, beast of burden, zoo animal, agriculturally or economically significant animal. As will be appreciated, given the aesthetic and functional advantages of the present compositions as disclosed herein it is the primary intention that the compositions are formulated so as to be useful in application to humans, and in particular the skin of the face or upper torso.

The composition may be used in a dermatologically effective amount, which refers to that amount which, when administered dermatologically (i.e., topically) to an animal, is sufficient to effect the desired effect, such as the desired amount of hydration or the desired amount of an active substance carried by the composition. The amount of composition which constitutes a dermatologically effective amount may vary depending on, the condition of the skin and the need for improvement, and the age of the animal to be treated, but can be determined routinely by one of ordinary skill in the art having regard to his own knowledge and to this disclosure.

It will be appreciated that in the description of exemplary embodiments of the invention, various features of the invention are sometimes grouped together in a single embodiment, FIGURE, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following are hereby expressly incorporated into this Summary section, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. Steps may be added or deleted to methods described within the scope of the present invention.

Although the invention has been described with reference to specific examples, it will be appreciated by those skilled in the art that the invention may be embodied in many other forms.

The present invention will now be more fully described by reference to the following non-limiting preferred embodiments.

EXAMPLES

Commercial evaporators such as the Alfa Laval, consist of smaller effects, or evaporators in series. Juices typically move along one effect and then to the next and the next, until such time that the juice has been concentrated to the desired final brix level. In the process of dehydration, water is removed from each of these effects. In the evaporator mentioned, there are four effects. Effect 1 evaporates the incoming juice firstly and concentrates the juice, before it moves to effect 2, effect 3 and finally effect 4. There can be less or more effects in any given evaporator. Often, juices are concentrated until they reach from between 40 and 70 Brix, depending on the juice processed.

When using commercial evaporators, fractionation involves removal of water from the different effects during juice concentration, a process that produces water with different amounts of heavy or light water ratios or composition.

Concentrates vary in brix (One degree Brix is 1 grain of sucrose in 100 grams of solution and represents the strength of the solution as percentage by mass), ranging from 40 (carrots) to 65 and 70 (apple juice, orange juice).

Water extracted as a result of concentrating carrot juice from 10 to 40 brix, using the Alfa Laval series evaporator, produced an aqueous fraction that had a delta-O-18 ratio of between −4.21 and −4.88. This ratio represents the pooling of condensate from all of the 4 in series effects (Sample 1, Table 1). This approach is divergent from prior art methods which teach the production of water from such pooled condensate that is produced by all the effects As an example to demonstrate the process of fractionation of condensate and how it can affect the delta-O-18 ratio, fresh carrot juice was used. This juice was used for:

1. Concentrating carrot juice commercially from 10 Brix to a liquid concentrate with 42 Brix using the Alfa Laval 4 effect in series evaporator (Table 1, Sample 1).
2. Further concentrating, the already, commercial carrot concentrate from 40 brix to 65 brix and collecting the condensate (Table 1, Sample 2).
3. Condensate removed from Effect 1 from Alfa Laval concentrator during carrot concentrate production (Table 1, Sample 4).
4. Condensate removed from Effect 2 from Alfa Laval concentrator during carrot concentrate production (Table 1, Sample 5).
5. Condensate removed from Effect 3 from Alfa Laval concentrator during carrot concentrate production (Table 1, Sample 6).

6. Condensate removed from Effect 4 from Alfa Laval concentrator during carrot concentrate production (Table 1, Sample 7).

This study demonstrated the following:
1. Comparing the delta-O-18 ratio of samples 1 and 2, Table 1, revealed that condensate removed from carrot juice during the process of concentrating from 10 to 40 brix, produced water that had lower heavy water ratios relative to light water. If the 40 Brix concentrate was further dehydrated to 65 brix, using the Buchi Rotavapor R-200 unit, then the condensate became enriched in heavy water, suggesting earlier dehydration preferentially removed the light water.
2. Carrot juice concentration using the Alfa Laval concentrator flows from effect 1 to effect 4 in series and becomes concentrated from 10 to 40 brix. It was shown (Table 3, Samples 4, 5, 6, and 7), that the condensate heavy water content began increasing at each evaporator effect, from order 1 to 4.

In another study, it was found that removing most of the water from sugar cane juice to obtain a molasses, produced a condensate with a Delta O18‰ VSMOW value of −2.1. Such a value suggests this fraction is very high in heavy water (Table 1, Sample 3). This was carried out to show that if most of the aqueous fraction was removed during evaporation or concentration, rather than just a portion of it, then the condensate would retain the high ratio of heavy water as found in the original sugar cane juice.

To carry out experiments in the laboratory, a Buchi Rotavapor R-200 vacuum, heat distiller (FIG. 1) was used. Briefly, juice volume is aspirated into flask F, through tube A as a result of lower pressure within vessel. The heat bath G was set at around 80 Celsius and the flask F was submerged into the hot water bath so that the juice level was below the water level in the heat bath G. The flask F was continually rotated using an electric motor C, throughout the duration of distillation. Distillate entered the cooling coil B and was condensed using circulating coolant and the distillate was collected in flask E.

TABLE 1

Delta O18 VSMOW of fractionated and non-fractionated carrot juice.

| Sample No. | Water Source | Delta O18 % VSMOW | comments |
|---|---|---|---|
| 1 | Final condensate removed during commercial carrot juice concentration from 10 brix to 40 brix | −4.47/ −4.42/ −4.88 | Carrot juice (10 Brix) was commercially concentrated to 40 Brix in the process using an Alfa Laval concentrator. |
| 2 | Condensate from 40 Brix carrot juice concentrate, further evaporated to 65 Brix. | −1.21 | Initially concentrated using Alfa Laval concentrator to 40 Brix. Then this carrot concentrated was further concentrated from 40 brix to 65 brix in a laboratory vacuum distillation Buchi Rotavapor R-200 unit. |
| 3 | Unfractionated condensate removed from sugar cane juice, in the production of Molasses | −2.11 | 90% water removed, molasses remaining. Carried out by ISIS sugar refinery Queensland Australia. |
| 4 | Condensate removed from Effect 1 from Alfa Laval concentrator during carrot concentrate production. | −6.4 | 1 of 4 effects. Effect 1 is first condensate removed from neat carrot juice, during the process of concentrating from 10 to 40 brix. |
| 5 | Condensate removed from Effect 2 from Alfa Laval concentrator during carrot concentrate production. | −6.21 | 2 of 4 effects. Effect 2 is second condensate removed from carrot juice, during the process of concentrating from 10 to 40 brix. |
| 6 | Condensate removed from Effect 3 from Alfa Laval concentrator during carrot concentrate production. | −4.96 | 3 of 4 effects. Effect 3 is third condensate removed from carrot juice, during the process of concentrating from 10 to 40 brix. |
| 7 | Condensate removed from Effect 4 from Alfa Laval concentrator during carrot concentrate production. | −4.12 | 4 of 4 effects. Effect 4 is the last condensate removed from carrot juice, during the process of concentrating from 10 to 40 brix. |

The invention claimed is:

1. A process for preparing a beverage comprising steps of:
obtaining water from plant material;
processing the plant material in a commercial juice producing process into a juice comprising water and solids;
evaporating the juice in an evaporation process;
when the juice has a water content of 30% or less, capturing the evaporated water by a condenser to produce the beverage; and
enriching the beverage in at least one of oxygen isotopes;
wherein the at least one of oxygen isotopes is in a range of:
for isotope 16O: 0.99738 to 0.99776 mole fraction;
for isotope 17O: $3.7 \times 10^{-4}$ to $4.0 \times 10^{-4}$ mole fraction; and
for isotope 18O: $1.88 \times 10^{-3}$ to $2.22 \times 10^{-3}$ mole fraction.

2. The process of claim 1, further comprising adding a vitamin to the beverage, wherein the vitamin comprises at least one of:
vitamin C, vitamin B1, vitamin B2, niacin, vitamin B6, folate, vitamin B12, biotin and pantothenic acid.

3. The process of claim 1, further comprising adding a food grade additive to the beverage, wherein the food grade additive comprises at least one of: a buffer, a food acid, and a food base.

4. The process of claim 3, wherein adding the food grade additive to the beverage further comprises at least one of: a carbohydrate, an amino acid, a peptide, a protein, a protein hydrosylate, a mineral, a fat, an oil, a plant extract and an animal extract.

5. A process for preparing a topical dermatological composition comprising steps of:
obtaining water from plant material;
processing the plant material during a commercial juice-producing process into a juice comprising water and solids;
evaporating the juice in an evaporation process during the commercial juice-producing process, and when the juice has a water content of 30% or less, condensing the evaporated water with a condenser to form a condensate;
forming the topical dermatological composition from the condensate; and enriching the topical dermatological composition in at least one of oxygen isotopes;
wherein the at least one of oxygen isotopes is in a range of:
for isotope 16O: 0.99738 to 0.99776 mole fraction;
for isotope 17O: $3.7 \times 10^{-4}$ to $4.0 \times 10^{-4}$ mole fraction; and
for isotope 18O: $1.88 \times 10^{-3}$ to $2.22 \times 10^{-3}$ mole fraction.

6. The process of claim 5, further comprising adding a vitamin to the topical dermatological composition, wherein the vitamin is at least one of: vitamin A, vitamin C, vitamin E, and vitamin K.

7. The process of claim 5, further comprising adding a dermatologically acceptable excipient to the topical dermatological composition, wherein the dermatologically acceptable excipient includes at least one of: an adjuvant, a carrier, a glidant, a diluent, a preservative, a dye or colorant, a surfactant, a wetting agent, a dispersing agent, a suspending agent, a stabilizer, an isotonic agent, a solvent, and an emulsifier.

8. The process of claim 5, further comprising adding a salt to the topical dermatological composition, wherein the salt comprises salts derived from inorganic bases including at least one of: sodium, potassium, lithium, ammonium, calcium, magnesium, iron, zinc, copper, manganese, and aluminum salts.

9. The process of claim 5, further comprising adding a salt to the topical dermatological composition, wherein the salt comprises: salts derived from organic bases including at least one of: salts of primary, secondary, and tertiary amines, substituted amines including naturally occurring substituted amines, cyclic amines and basic ion exchange resins including, but not limited to: ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, and polyamine resins.

10. The process of claim 5, further comprising adjusting a pH of the composition to between about 6.0 and about 8.0.

11. The process of claim 10, further comprising adjusting the pH by use of citric acid.

12. The process of claim 5, further comprising adding a buffer to the topical dermatological composition, wherein the buffer comprises at least one of: 1,6-hexanediamine, 2-aminobutanol, acetic acid, acetyl mandelic acid, adipic acid, alstonia scholaris bark extract, aluminum glycinate, aluminum lactate, aluminum triformate, aminoethyl propanediol, aminomethyl propanediol, aminomethyl propanol, aminopropanediol, ammonia, ammonium acetate, ammonium bicarbonate, ammonium carbamate, ammonium carbonate, ammonium chloride, ammonium glycolate, ammonium hydroxide, ammonium lactate, ammonium molybdate, ammonium nitrate, ammonium phosphate, ammonium thiocyanate, ammonium vanadate, ascorbic acid, azelaic acid, babassu acid; bakuhan; benzilic acid, bis-hydroxyethyl tromethamine, bismuth citrate, boric acid, butyl diethanolamine, calcium carbonate, calcium citrate, calcium dihydrogen phosphate, calcium glycinate, calcium hydroxide, calcium lactate, calcium oxide, calcium phosphate, citric acid, clay minerals, copper glycinate, diammonium citrate, diammonium phosphate, dibutyl ethanolamine, diethyl ethanolamine, dimethyl isopropanolamine, dimethyl mea, dioleoyl edetolmonium methosulfate, dioleyl phosphate, dipotassium phosphate, disodium fumarate, disodium phosphate, disodium pyrophosphate, disodium tartrate, ethanolamine, ethanolamine HCL, ethyl ethanolamine, fumaric acid, galacturonic acid, glucoheptonic acid, gluconic acid, glucuronic acid, glutaric acid, glycine, glycolic acid, glyoxylic acid, guanidine carbonate, guanidine HCl, hydrobromic acid, hydrochloric acid, hydroxyectoin, hydroxyethylpiperazine ethane sulfonic acid, imidazole, isobutyric acid, isopropanolamine, isopropylamine, lactic acid, lactobionic acid, lauryl p-cresol ketoxime, lithium carbonate, lithium hydroxide, magnesium acetate, magnesium carbonate hydroxide, magnesium glycinate, magnesium hydroxide, magnesium lactate, magnesium oxide, maleic acid, malic acid, malonic acid, maltobionic acid mea-borate, metaphosphoric acid, methoxy peg-100/polyepsilon caprolactone ethylhexanoate; methoxypeg-100/polyepsilon caprolactone palmitate; methoxy peg-114/polyepsilon caprolactone; methylethanolamine, monosodium citrate, mudstone powder; paecilomyces japonica/grape/cucumber juice extract ferment filtrate; pentapotassium triphosphate, pentasodium triphosphate, phenolsulfonphthalein, phenyl mercuric borate, phosphonobutanetricarboxylic acid, phosphoric acid, phosphorus pentoxide, potassium bicarbonate, potassium biphthalate, potassium bitartrate, potassium borate, potassium carbonate, potassium citrate, potassium hydroxide, potassium lactate, potassium magnesium aspartate, potassium oxide, potassium phosphate, potassium sodium tartrate, potassium tartrate, propane tricarboxylic acid, quinic acid, ribonic acid, sebacic acid, sesquiethoxytriethanolamine; sh-decapeptide-7; sodium acetate, sodium aluminate, sodium aluminum lactate, sodium arachidate; sodium aspartate, sodium bicarbonate, sodium bisulfate, sodium borate, sodium butoxyethoxy acetate, sodium calcium boron phosphate; sodium calcium copper phosphate; sodium calcium zinc phosphate; sodium carbonate, sodium citrate, sodium esylate, sodium formate, sodium fumarate, sodium glycolate, sodium humate, sodium hydroxide, sodium lactate, sodium metaphosphate, sodium metasilicate, sodium oxide, sodium phosphate, sodium sesquicarbonate, sodium silicate, sodium succinate, sodium trimetaphosphate, strontium hydroxide, succinic acid, sulfuric acid, tartaric acid, taurine, tea-diricinoleate/ipdi copolymer, tea-hydroiodide, tea-sulfate, tetrahydroxyethyl ethylenediamine, tetrapotassium pyrophosphate, tetrasodium pyrophosphate, triethanolamine, triisopropanolamine, trisodium phosphate, trisodium sulfosuccinate, Triticum vulgare protein, Triticum vulgare seed extract, tromethamine, urea, uric acid, zinc carbonate hydroxide, zinc glycinate, zinc hexametaphosphate, and zinc magnesium aspartate.

13. The process of claim 5, further comprising:
adding a surfactant to the topical dermatological composition, wherein the surfactant includes at least one of: an anionic surfactant, a cationic surfactant, a nonionic surfactant, a zwitterionic surfactant, and an amphoteric surfactant.

14. The process of claim 5, further comprising:
adding a viscosity increasing agent to the topical dermatological composition, wherein the viscosity increasing agent includes at least one of the following: a gum, a gel, an agar and a hydrogel.

15. The process of claim 5, further comprising:
adding a transdermal pharmaceutical substance to the topical dermatological composition.

16. The process of claim 5, further comprising:
adding a detergent to the topical dermatological composition.

17. The process of claim 5, further comprising:
adding an anti-bacterial composition to the topical dermatological composition.

18. The process of claim 5, further comprising concentrating or fractionating the water by at least one of: nanofiltration, reverse osmosis, forward osmosis, and membrane distillation.

19. A process for preparing a beverage comprising steps of:
deriving an aqueous fraction of water from liquefied plant material as a by-product of a commercial juice-producing process; wherein the liquefied plant material has a water content of 30% or less, wherein the aqueous fraction of water is lower in heavy water than light water;
subjecting the aqueous fraction of water to a multiple effect evaporator;
obtaining a distilled fraction after the aqueous fraction of water is subject to the multiple effect evaporator;
enriching the distilled fraction with a heavy water isotope in a range between 1 molecule per 10 total molecules and 1 molecule per 1000000 total molecules;
wherein the heavy water isotope is in a range of:
for isotope 16O: 0.99738 to 0.99776 mole fraction;
for isotope 17O: $3.7 \times 10^{-4}$ to $4.0 \times 10^{-4}$ mole fraction; and
for isotope 18O: $1.88 \times 10^{-3}$ to $2.22 \times 10^{-3}$ mole fraction; and
adding a food grade additive, wherein the food grade additive comprises at least one of a coloring agent, a flavoring agent, an electrolyte, a sweetener, a preservative, a dissolved gas, an undissolved gas, a nutrient, a vitamin, a pharmaceutical agent, a probiotic and a prebiotic.

20. A process for preparing a beverage comprising steps of:
liquefying plant material during a commercial juice producing process to produce a juice comprising water and solids;
concentrating the juice through evaporation until the juice has a water content of about 30%;
further concentrating the juice through evaporation until the juice has a water content of less than 30% down to 1% and substantially only solid material remains after the concentrating steps;
condensing evaporate from the further concentrating of the juice with a condenser;
collecting the condensed evaporate as captured water;
producing the beverage from the captured water, wherein the beverage is enriched in at least one of oxygen isotopes;
wherein the at least one of oxygen isotopes is in a range of:
for isotope 16O: 0.99738 to 0.99776 mole fraction;
for isotope 17O: $3.7 \times 10^{-4}$ to $4.0 \times 10^{-4}$ mole fraction; and
for isotope 18O: $1.88 \times 10^{-3}$ to $2.22 \times 10^{-3}$ mole fraction.

\* \* \* \* \*